United States Patent
Mori et al.

(10) Patent No.: US 7,914,867 B2
(45) Date of Patent: Mar. 29, 2011

(54) MEDICAL GAS BARRIER FILM AND MEDICAL BAG USING THE SAME

(75) Inventors: Hitoshi Mori, Tokushima (JP); Yasushi Morimoto, Naruto (JP); Kenji Konishi, Tokushima (JP); Isamu Tateishi, Naruto (JP)

(73) Assignee: Otsuka Pharmaceutical Factory, Inc., Tokushima (JP)

( * ) Notice: Subject to any disclaimer, the term of this patent is extended or adjusted under 35 U.S.C. 154(b) by 0 days.

(21) Appl. No.: 11/665,384

(22) PCT Filed: Oct. 13, 2005

(86) PCT No.: PCT/JP2005/018834
§ 371 (c)(1),
(2), (4) Date: Apr. 13, 2007

(87) PCT Pub. No.: WO2006/043459
PCT Pub. Date: Apr. 27, 2006

(65) Prior Publication Data
US 2008/0063825 A1    Mar. 13, 2008

(30) Foreign Application Priority Data
Oct. 18, 2004   (JP) ................... 2004-302987

(51) Int. Cl.
*B32B 1/02*     (2006.01)
*B32B 27/00*    (2006.01)
*B32B 27/32*    (2006.01)
*B32B 27/34*    (2006.01)
*B32B 27/36*    (2006.01)
*B32B 27/25*    (2006.01)

(52) U.S. Cl. ............ 428/35.2; 428/34.1; 428/34.2; 428/34.3; 428/35.7; 428/35.9; 428/474.4; 428/477.7; 428/480; 428/483; 428/500; 428/515

(58) Field of Classification Search .......... 428/34.1, 428/34.2, 35.7, 35.9, 34.3, 35.2, 474.4, 477.7, 428/480, 483, 500, 515
See application file for complete search history.

(56) References Cited

U.S. PATENT DOCUMENTS
5,520,972 A    5/1996   Ezaki et al.
(Continued)

FOREIGN PATENT DOCUMENTS
DE     19633641    *   2/1998
(Continued)

OTHER PUBLICATIONS
Office Action dated Dec. 9, 2010 in corresponding Japanese application No. 2006-542925.

*Primary Examiner* — Marc A Patterson
(74) *Attorney, Agent, or Firm* — Finnegan, Henderson, Farabow, Garrett & Dunner, L.L.P.

(57) ABSTRACT

The object of the present invention is to provide a gas barrier film suitable for medical uses, which is excellent in gas and vapor properties and can prevent ingredients of an adhesive and the like from eluting even after heating and sterilizing treatment, and a medical bag using the gas barrier film. A medical gas barrier film of the present invention comprises a multilayer gas barrier film 10 including a deposition oriented polyester layer 11 having a deposited layer 13 of an inorganic oxide on one surface, an oriented polyamide layer 15 adhered to the surface of the deposited layer 13 and a polyethylene layer 17 adhered to the surface on the opposite side to an adhered surface 15a of the oriented polyamide layer 15, and a multilayer substrate film 22 including a cyclic olefin polymer layer 25, an elastomer layers 24, 26 and a heat sealing layer 23, and the multilayer substrate film 22 is adhered to an other surface 11b on the opposite side of the deposited layer of the deposition oriented polyester layer 11.

9 Claims, 3 Drawing Sheets

U.S. PATENT DOCUMENTS

| | | | |
|---|---|---|---|
| 5,792,526 A | 8/1998 | Watanabe et al. | |
| 6,165,573 A | 12/2000 | Hirose et al. | |
| 6,306,473 B1 | 10/2001 | Denpou et al. | |
| 6,379,812 B1 * | 4/2002 | Hofmeister et al. | 428/474.4 |
| 6,503,587 B2 * | 1/2003 | Kashiba et al. | 428/35.7 |
| 2005/0208240 A1 | 9/2005 | Manabe et al. | |

FOREIGN PATENT DOCUMENTS

| | | |
|---|---|---|
| EP | 0 968 817 A2 | 1/2000 |
| JP | 60-55958 | 1/1985 |
| JP | 1-279042 | 11/1989 |
| JP | 1-308624 | 12/1989 |
| JP | 5-4638 | 1/1993 |
| JP | 5-293160 | 9/1993 |
| JP | 5-293159 | 11/1993 |
| JP | 7-096589 | 4/1995 |
| JP | 9-011416 | 1/1997 |
| JP | 11-70624 | 3/1999 |
| JP | 2000-052515 | 2/2000 |
| JP | 2000-309770 | 11/2000 |
| JP | 2000-351953 | 12/2000 |
| JP | 2001-157705 | 6/2001 |
| JP | 2001-162724 A | 6/2001 |
| JP | 2001-315276 | 11/2001 |
| JP | 2002-155260 | 5/2002 |
| JP | 2003-267454 | 9/2003 |
| JP | 2004-58336 | 2/2004 |
| JP | 2004-121824 | 4/2004 |
| JP | 2004-148681 | 5/2004 |
| JP | 2004-231199 | 8/2004 |

* cited by examiner

MEDICAL GAS BARRIER FILM AND MEDICAL BAG USING THE SAME

TECHNICAL FIELD

The present invention relates to a gas barrier film suitable for medical applications and capable of maintaining excellent gas and vapor barrier properties and restricting elution of compounding ingredients of the film and ingredients of an adhesive without impairing flexibility, transparency and impact resistance of the film even after heating and sterilizing treatment and long storage, and a medical bag using the gas barrier film.

BACKGROUND ART

Plastic bags such as infusion solution bags have advantages of easy handling and simple disposal after use. Currently, polyethylene as a safe material is generally used for plastic bags prevailing in the field of medical containers.

However, since polyethylene is a plastic having high gas permeability, when easily oxidized medicine such as amino acid is contained in a medical bag, the medical bag is generally held in a plastic outer bag having gas barrier property together with an oxygen absorber.

On the other hand, to reduce costs of the outer bag, there has been a demand to impart gas barrier property to the medical bag itself and various plastic materials having gas barrier property as well as properties including flexibility, transparency and impact resistance have been considered.

A plastic material described in Patent document 1 is characterized in that it is a multilayer film having a heat sealing resin layer, a biaxial oriented polyester resin film with an inorganic oxide deposited layer, a biaxial oriented polyamide resin film and a surface protective film, wherein the deposited layer of the biaxial oriented polyester resin film is adhered to the heat sealing resin layer, the surface on the opposite side to the deposited surface of the biaxial oriented polyester resin film is adhered to one surface of the biaxial oriented polyamide resin film, and the surface protective film is disposed on the other surface of the biaxial oriented polyamide resin film.

A plastic material described in Patent document 2 is characterized in that it is a multilayer film having a polyethylene layer forming a heat sealing part, a cyclic olefin polymer layer and a polyethylene terephthalate layer with an inorganic oxide deposited layer, wherein the polyethylene layer is adhered to one surface of the cyclic olefin polymer layer and the deposited layer of the polyethylene terephthalate layer is adhered to the other surface of the cyclic olefin polymer layer.

A plastic material described in Patent document 3 is characterized in that it is a multilayer film having a heat sealing layer (ethylene polymer), a biaxial oriented film (biaxial oriented polyethylene) substrate with an inorganic oxide deposited layer and a protective film (biaxial oriented polyamide film), wherein the heat sealing layer is adhered to the surface on the opposite side to the inorganic oxide deposited layer of the biaxial oriented film substrate, and the protective film is adhered to the surface of the inorganic oxide deposited layer of the biaxial oriented film substrate.

[Patent document 1] Japanese Unexamined Patent Publication No. 2004-58336
[Patent document 2] Japanese Unexamined Patent Publication No. 2001-157705
[Patent document 3] Japanese Unexamined Patent Publication No. 2004-148681

DISCLOSURE OF THE INVENTION

Problems to be Solved by the Invention

Medical bags require, for example, heat resistance to heating and sterilizing treatment and safety to drugs contained therein (especially, low elution behavior of compounding ingredients of a resin film and ingredients of an adhesive) in addition to properties such as flexibility, transparency and impact resistance, which are required for conventional plastic bags. However, in the present circumstances, a plastic material which fulfills all of the properties has not been found.

The multilayer films disclosed in Patent documents 1 to 3 have a common problem that flexibility is low and thus creases and lines are easy to generate when an infusion solution bag or the like is formed of the films.

Further, the multilayer films described in Patent documents 1 and 2 have the problem that gas and vapor barrier properties are easy to lower over time since the deposited layer of the polyester (polyethylene terephtalate) film substrate is disposed at the side of an inner surface of a packaging body using the multilayer films. The multilayer films described in Patent documents 1 and 3 have the problem that the adhesive used for adhesion between the layers is eluted. In the multilayer films described in Patent documents 2 and 3, since the thickness between an outer surface of a packaging body using the multilayer films and the deposited layer is small, gas and vapor properties can lower over time.

An object of the present invention is to provide a gas barrier film suitable for medical applications capable of realizing excellent gas and vapor barrier properties while maintaining flexibility, transparency and impact resistance of the film and controlling elution of compounding ingredients of the film and ingredients of an adhesive even after heating and sterilizing treatment and long storage, and a medical bag using the gas barrier film.

Means for Solving Problems

To solve the above-mentioned problems, the present invention provides
(1) a medical gas barrier film comprising a multilayer gas barrier film and a multilayer substrate film adhered to the multilayer gas barrier film, wherein the multilayer gas barrier film includes a deposition oriented polyester layer having a deposited layer of an inorganic oxide on one surface, an oriented polyamide layer adhered to the surface of the deposited layer of the deposition oriented polyester Layer and a polyethylene layer adhered to the surface on the opposite side to the adhered surface of the oriented polyamide layer to the deposited layer, the multilayer substrate film includes a cyclic olefin polymer layer, an elastomer layer and a heat sealing layer and is adhered to the other surface of the deposition oriented polyester layer, and the heat sealing layer is disposed on the surface on the opposite side to the adhered surface of the multilayer substrate film to the deposition oriented polyester layer,
(2) a medical gas barrier film as stated in the above (1), wherein the multilayer substrate film has a cyclic olefin polymer layer, a first elastomer layer adhered to one surface of the cyclic olefin polymer layer, a heat sealing layer on the opposite side to the adhered surface of the first elastomer layer to the cyclic olefin polymer layer, a second elastomer layer adhered to the other surface of the cyclic olefin polymer layer and a polyethylene layer adhered to the surface on the opposite side to the adhered surface of the second elastomer layer to the cyclic olefin polymer layer, (3) a medical gas barrier film as stated in the above (2), wherein the total thickness of the first elastomer layer and the second elastomer layer is 55 to 80% of the thickness of the multilayer substrate film, (4) a medical gas barrier film as stated in the above (1), wherein the thickness of the polyethylene layer of the multilayer gas barrier film is 1 or 2 times larger than the total thickness of the deposition oriented polyester layer and the oriented polyamide layer, (5) a medical gas barrier film as stated in the above (1), wherein the polyethylene layer of the multilayer gas barrier film is a three-layer film formed of a linear polyethylene film having a density of 0.910 to 0.930 g/cm$^3$ and high density polyethylene films each having a density of 0.950 to 0.970 g/cm$^3$ and adhered to both surfaces of the linear polyethylene layer, and the thickness of each high density polyethylene film is 0.2 to 0.3 time larger than that of the linear polyethylene film, (6) a medical gas barrier film as stated in the above (1), wherein the inorganic oxide is alumina, (7) a medical gas barrier film as stated in the above (1), wherein the multilayer substrate film is a cylindrical film formed by inflation molding and an innermost layer of the cylindrical film is the heat sealing layer, (8) a medical bag formed by welding a medical gas barrier film so that heat sealing layers thereof face each other, wherein the medical gas barrier film comprises a multilayer gas barrier film and a multilayer substrate film adhered to the multilayer gas barrier film, the multilayer gas barrier film includes a deposition oriented polyester layer having a deposited layer of an inorganic oxide on one surface, an oriented polyamide layer adhered to the surface of the deposited layer of the deposition oriented polyester layer and a polyethylene layer adhered to the surface on the opposite side to the adhered surface of the oriented polyamide layer to the deposited layer, the multilayer substrate film includes a cyclic olefin polymer layer, an elastomer layer and a heat sealing layer and is adhered to the other surface of the deposition oriented polyester layer, and the heat sealing layer is disposed on the surface on the opposite side to the adhered surface of the multilayer substrate film to the deposition oriented polyester layer, (9) a medical bag formed by welding an open end of a multilayer substrate film in a medical gas barrier film, wherein the medical gas barrier film comprises a multilayer gas barrier film and a multilayer substrate film adhered to the multilayer gas barrier film, the multilayer gas barrier film includes a deposition oriented polyester layer having a deposited layer of an inorganic oxide on one surface, an oriented polyamide layer adhered to the surface of the deposited layer of the deposition oriented polyester layer and a polyethylene layer adhered to the surface on the opposite side to the adhered surface of the oriented polyamide layer to the deposited layer, the multilayer substrate film is a cylindrical film formed by inflation molding, includes a cyclic olefin polymer layer, an elastomer layer and a heat sealing layer and is adhered to the other surface of the deposition oriented polyester layer, the heat sealing layer is disposed on the surface on the opposite side to the adhered surface of the multilayer substrate film to the deposition oriented polyester layer, and an innermost layer of the cylindrical multilayer substrate film is the heat sealing layer,

(10) a medical bag as stated in the above (8), the whole of which is subjected to heating and sterilization after being filled with a medical fluid and sealed, and

(11) a medical bag as stated in the above (9), the whole of which is subjected to heating and sterilization after being filled with a medical fluid and sealed.

EFFECTS OF THE INVENTION

A gas barrier film according to the present invention can obtain excellent gas and vapor barrier properties while maintaining flexibility, transparency and impact resistance of the film, and suppress degradation of gas and vapor barrier properties with time due to heating and sterilizing treatment and long storage as well as elution of compounding ingredients of the film and ingredients of an adhesive.

BEST MODE FOR CARRYING OUT THE INVENTION

Figure 1:
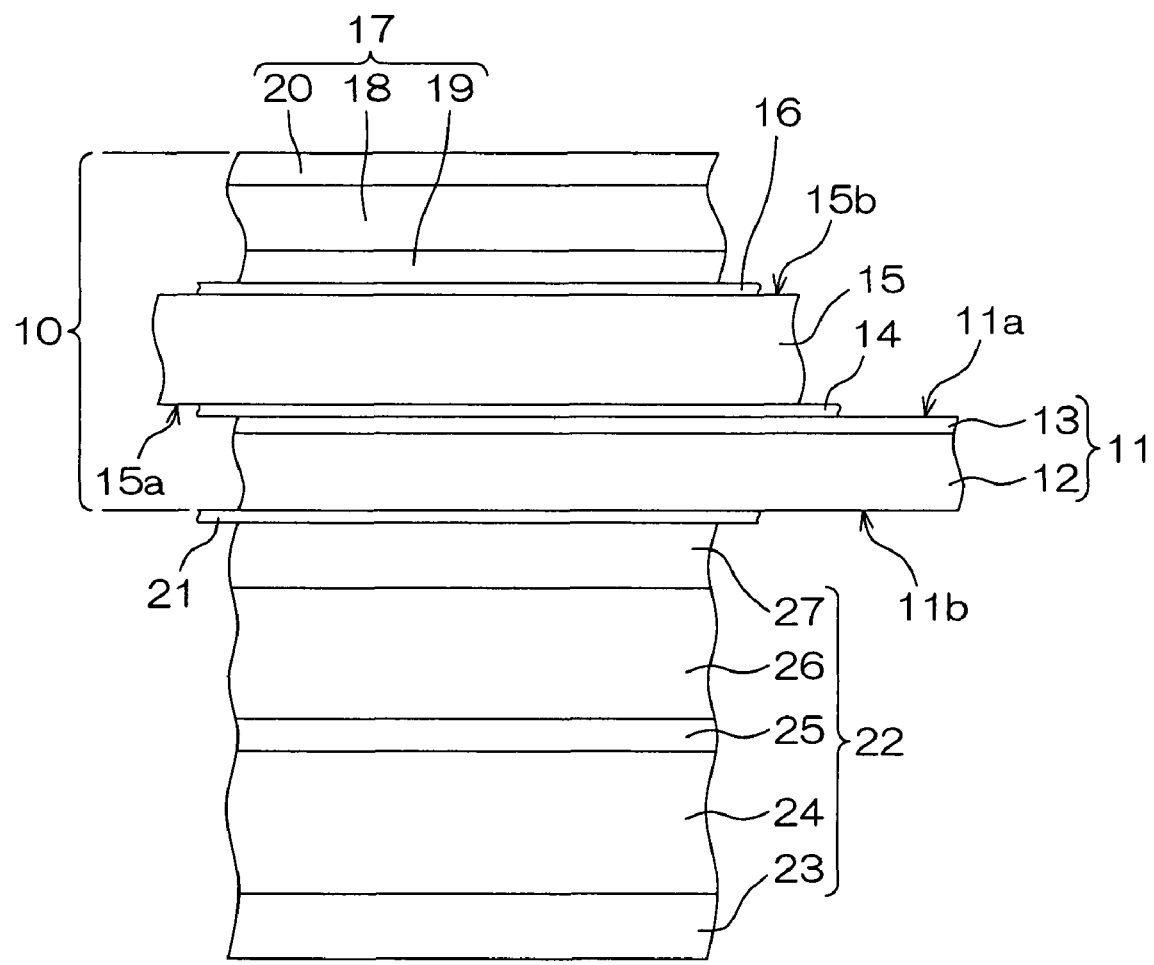
FIG. 1 is a schematic sectional view showing the configuration of layers of a medical gas barrier film in accordance with an embodiment.

A medical gas barrier film of the present invention comprises (i) a multilayer gas barrier film including an deposition oriented polyester layer having an inorganic oxide deposited layer on one surface thereof, an oriented polyamide layer adhered to the surface of the deposited layer and a polyethylene layer adhered to the surface on the opposite side to the adhered surface of the oriented polyamide layer to the deposited layer, and (ii) a multilayer substrate film including a cyclic olefin polymer layer, an elastomer layer and a heat sealing layer, and the above (ii) multilayer substrate film is adhered to the other surface of the deposition oriented polyester layer in the above (i) multilayer gas barrier film, and the heat sealing layer in the above (ii) multilayer substrate film is disposed on the surface on the opposite side to the surface adhered to the deposition oriented polyester layer.

As described above, the multilayer gas barrier film includes three layers of the layer formed of the deposition oriented polyester film having the inorganic oxide deposited layer on one surface thereof (hereinafter, referred to as "deposition oriented polyester layer"), the oriented polyamide layer adhered to the surface of the deposited layer of the deposition oriented polyester layer and the polyethylene layer adhered to the surface on the opposite side to the adhered surface of the oriented polyamide layer to the deposited layer.

The deposition oriented polyester layer is, for example, a layer formed to impart gas barrier property to the whole medical gas barrier film and is made by forming the inorganic oxide deposited layer on the surface of the polyester film subjected to orienting treatment.

Polyesters for the oriented polyester film include polyethylene terephthalate (PET), polybutylene terephthalate (PBT), polyethylene napthalate (PEN) and polybutylene napthalate (PBN).

Orienting treatment of the polyester film may be either uniaxial orientation or biaxial orientation. Specific techniques of biaxial orienting treatment include tubular biaxial orientation and tenter biaxial orientation. By applying orienting treatment to the polyester film, pinhole resistance, strength, heat resistance in evaporating treatment, surface smoothness of the film and the like can be improved.

Inorganic oxides forming the deposited layer include alumina (aluminum oxide), silica (silicon oxide), magnesium oxide and titan oxide, for example. Especially, alumina is preferable in terms of transparency of the deposited layer.

Specific examples of the deposition oriented polyester film having the deposited layer made of alumina (hereinafter, referred to as "alumina deposition oriented polyester film") include transparent barrier films manufactured by Toppan Printing Co., Ltd. (product name "GL FAMILY"; "GL-AEH" (substrate: PET), "GL-AU" (substrate: PET), "GL-AE" (substrate: PET)) and transparent barrier films manufactured by Toray Advanced Film Co., Ltd. (product name "BARRIER ROCKS" series; "1011RG", "1011HG", "1031HG", and so on).

The ratio of the deposition oriented polyester layer to the multilayer gas barrier film in thickness is preferably 15 to 35%, more preferably 10 to 30%, and the ratio of the deposition oriented polyester layer to the entire medical gas barrier film in thickness is preferably 3 to 10%, more preferably 5 to 7%. The thickness of the deposition oriented polyester layer is preferably 7 to 20 µm, more preferably 9 to 15 µm.

The oriented polyamide layer is, for example, a layer formed to protect the deposited layer of the deposition oriented polyester layer and is made using a polyamide film subjected to orienting treatment.

Polyamides for the oriented polyamide film include nylon-6, nylon-6,6, nylon-6,10, nylon-6,12, nylon-11 and nylon-12.

Orienting treatment of the polyamide film may be either uniaxial orientation or biaxial orientation. Specific techniques of biaxial orienting treatment include tubular biaxial orientation and tenter biaxial orientation, for example. By applying orienting treatment to the polyamide film, pinhole resistance, strength, heat resistance in evaporating treatment, surface smoothness of the film and the like can be improved.

Specific examples of the oriented polyamide film include biaxial oriented nylon films manufactured by Unitica Ltd. (product name "EMBLEM" (registered trademark) series; "EMBLEM ONMB", and so on).

The ratio of the oriented polyamide layer to the multilayer gas barrier film in thickness is preferably 15 to 35%, more preferably 20 to 30%, and the ratio of the oriented polyamide layer to the entire medical gas barrier film in thickness is preferably 3 to 10%, more preferably 5 to 10%. The thickness of the oriented polyamide layer is preferably 7 to 20 µm, more preferably 10 to 15 µm.

The polyethylene layer in the multilayer gas barrier film is an outermost layer of a medical bag in the case where the medical bag is formed using the medical gas barrier film of the present invention, and for example, a layer formed to protect the surface of the medical gas barrier film and add soft touch to the medical gas barrier film.

The polyethylene film forming the polyethylene layer is not limited by density range such as high density and low density, molecular structure such as straight chain, and manufacturing methods such as high-pressure process and low-pressure process, and various polyethylene films may be used.

The polyethylene film may be formed of one type of polyethylene or a composite of two or more types of polyethylene.

Further, the polyethylene film may be a multilayer film formed of two or more types of polyethylene. Specific examples of the multilayer film include a three-layer film in which high density polyethylene having a density of 0.950 to 0.970 g/cm$^3$ is disposed on both surfaces of a linear polyethylene film having a density of 0.910 to 0.930 g/cm$^3$.

When the above-mentioned three-layer film is used as the polyethylene film forming the polyethylene layer, properties such as formability and strength of the medical gas barrier film of the present invention can be further improved. The ratio of the high density polyethylene in the three-layer film to the linear polyethylene in thickness is preferably 0.2 to 0.3, more preferably 0.22 to 0.28.

The thickness of the polyethylene layer is preferably 1 to 2 times, more preferably 1.2 to 1.8 times, larger than that of the sum of the alumina deposition oriented polyester layer and the oriented polyamide layer. The thickness of the polyethylene layer is preferably 5 to 30 µm.

The multilayer gas barrier film can be manufactured by separately molding three types of films of the alumina deposition oriented polyester layer, the oriented polyamide layer and the polyethylene layer and then laminating the films according to various laminating methods.

Various laminating methods can be adopted and a dry laminating method wherein an adhesive is used is the most preferable among them.

Although the thickness of the entire multilayer gas barrier film is not specifically limited, the thickness of 30 to 80 µm is preferable.

Various adhesives used for manufacture of the laminated film can be adopted as an adhesive used in the dry laminating method. The adhesives include "TAKELAC" series (product name "TAKELAC A315", etc.) and "TAKENATE" series (product name) manufactured by Mitsui Takeda Chemicals Co., Ltd.

The less the amount of ingredients of the adhesive eluted from the multilayer gas barrier film is, the better the adhesive is. Such adhesives include adhesives for dry lamination comprising at least a base compound and a stiffener, and the following combinations of the base compound and the stiffener are included (Refer to Japanese Unexamined Patent Publication No. 2000-309770, Japanese Unexamined Patent Publication No. 2000-351953 and Japanese Unexamined Patent Publication No. 2002-155260).

Base compound: polyether-polyurethane resin formed by extending a resin consisting of polyether and glycols and/or amines with diisocyanates; polyester resin formed of at least one type of acids selected from the group consisting of aromatic carboxylic acid, alicyclic carboxylic acid, aliphatic carboxylic acid and unsaturated carboxylic acid, esters or lactones of the above carboxylic acid and at least one type of glycols; polyester-urethane-diol resin formed by extending the above-mentioned polyester resin with diisocyanates; polyester resin formed of at least one type selected from the group consisting of dimer fatty acids and their esters and at least one type of glycols (at least one type of grycols selected from the group consisting of aromatic dicarboxylic acids and their ester compounds); polyester-urethane-diol resin formed by extending the polyester resin with diisocyanates; polyester-urethane-diol resin formed by extending the polyester diol resin formed of at least one type selected from the group consisting of dimer fatty acids, hydrogenated dimer fatty acids and ester and at least one type of glycols with diisocyanates.

Stiffener: isocyanates adduct of trimethylolpropane, buret or trimer of diisocyanates.

The multilayer gas barrier film can be manufactured by adopting an extrusion laminating method in place of the dry laminating method. In this case, an adhesive resin may be used in place of the above-mentioned adhesive and molding conditions of the publicly known extrusion laminating method can be employed.

Adhesive resins preferably include, for example, modified polyolefin obtained by graft copolymerizing polyolefin such as polyethylene with unsaturated carboxylic acid such as maleic acid, fumaric acid, tetrahydrophthalic adid, itaconic acid, citraconic acid, crotonic acid, isocrotonic acid, nagic acid, acrylic acid and methacryl acid or anhydrides of these acids.

As described above, the multilayer substrate film is provided on the other surface (the surface on the opposite side of the surface on which the deposited layer is formed) of the deposition oriented polyester layer in the multilayer gas barrier film, and is a laminated body having the cyclic olefin polymer layer, the elastomer layer and the heat sealing layer.

The cyclic olefin polymer layer is provided to prevent ingredients of the adhesive from exuding from the multilayer gas barrier film and permeation of moisture from exerting a negative impact such as peeling on the deposited layer of the deposition oriented polyester film, for example.

Cyclic olefin polymers forming the cyclic olefin polymer layer include, for example, a copolymer of ethylene and dicyclopentadiene compound, a copolymer of ethylene and norbornene compound, a ring-opened polymer of cyclopentadiene compound, a ring-opened copolymer of two or more types of cyclopentadiene compound and their hydrogenated polymers and copolymers.

In particular, the hydrogenated polymers and copolymers as saturated polymers among the above-mentioned cyclic olefin polymers are suitable for the material for the cyclic olefin polymer layer of the present invention since they are especially excellent in vapor barrier property and gas barrier property and also excellent in the effect of preventing absorption/adsorption of medicine, heat resistance, transparency, stability and the like.

The hydrogenated copolymer of ethylene and norbornene compound and the hydrogenated ring-opened polymer (copolymer) of one or two or more types of cyclopentadiene derivative are especially preferable among the above-mentioned cyclic olefin polymers.

Specific examples of the cyclic olefin polymers include a polymer having repeating unit shown in the following general formula (1) and repeating unit shown in the following general formula (1') and a polymer having repeating unit shown in the following general formula (2)

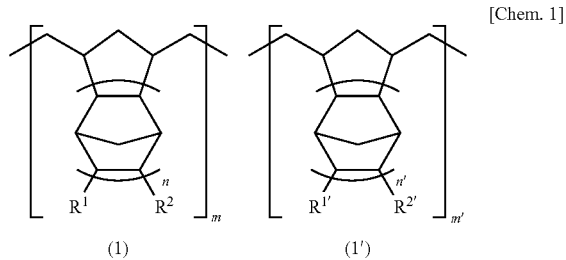

(1)  (1')

[Chem. 1]

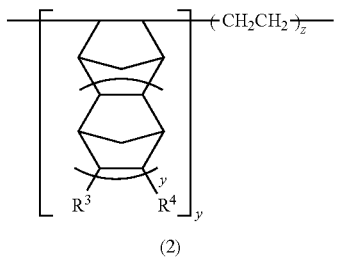

(2)

[Chem. 2]

(In the formulas, $R^1$, $R^{1'}$, $R^2$, $R^{2'}$, $R^3$ and $R^4$ independently indicate hydrogen atom, hydrocarbon residue, halogen atom, ester, and a polar group such as nitryl and pylidyl. $R^1$ and $R^2$, $R^1$ and $R^{2'}$ and $R^3$ and $R^4$ may be connected to each other to form a ring. m, m' x and z indicate an integer of 1 or more, and n, n' and y indicates an integer of 1 or more).

The polymer having the repeating units shown in the general formulas (1) and (1') is obtained by polymerizing one or two or more types of norbornene monomers according to a publicly known ring-opened polymerizing method or hydrogenating the ring-opened polymer thus obtained according to an ordinary method. On the other hand, the polymer having a structural unit shown in the general formula (2) is obtained by additive-copolymerizing one or two or more types of norbornene monomers and ethylene according to a publicly known method or hydrogenating the copolymer thus obtained according to an ordinary method.

Although the type of cyclic olefin polymer is not specifically limited, the glass transition temperature (Tg) thereof is preferably 70° C. or higher, more preferably 80 to 150° C. Although the molecular weight of cyclic olefin polymer is not specifically limited, the number molecular weight <Mn> measured according to gel permeation chromatography (GPC) analysis using cyclohexane as a solvent is preferably 10 to 100 thousand, more preferably 20 to 50 thousand. In the case where unsaturated bonding remaining in the molecular chain of cyclic olefin polymer is saturated by hydrogenation, although the hydrogenation ratio is not specifically limited, it is preferably 90% or more, more preferably 95% or more, even more preferably 99% or more.

Specific examples of the cyclic olefin polymers include cyclic olefin polymer manufactured by Mitsui Chemicals, Inc. (product name "APEL (registered trademark)" series), optical resin manufactured by JSR Corporation ("ARTON (registered trademark)"), general-purpose transparent engineering plastics manufactured by Zeon Corp., (product name "ZEONOR (registered trademark)" series) and "TOPAS (product name)" manufactured by Ticona GmbH.

In terms of compatibility with a layer adjacent to the cyclic olefin polymer layer (for example, an elastomer layer described later), mixed resin of cyclic olefin polymer and polyolefin resin may be used for the cyclic olefin polymer layer. The polyolefin resins include, for example, polyethylene (PE) homopolymer, copolymer of ethylene and α-olefins having a carbon number 3 to 12 (for example, butane-1, pentene-1, hexene-1, 4-methyl-1-pentene, octene-1, decene-1), polypropylene (PP) homopolymer, and copolymer of propylene and α-olefins having a carbon number 2 to 12 (for example, ethylene, butane-1, pentene-1, hexene-1,4-methyl-1-pentene, octene-1, decene-1). Above all, PE homopolymer is preferable. An example of a preferred mode of mixed resin of cyclic olefin polymer and polyolefin resin is that polyethylene having a density of 0.910 to 0.930 g/cm³ is mixed to cyclic olefin polymer by 5 to 40 weight %.

The ratio of the cyclic olefin polymer layer to the multilayer substrate film in thickness is preferably 3 to 10% and the ratio of the cyclic olefin polymer to the entire medical gas barrier film in thickness is 5 to 10%. The thickness of the cyclic olefin polymer layer is preferably 10 to 20 μm.

To protect hard and fragile cyclic olefin polymer, the elastomer layer is provided on the surface on each of both sides of the cyclic olefin polymer layer.

Elastomers for the elastomer layer include polyolefin elastomers, styrene elastomers and urethane elastomers, for example.

Polyolefin elastomers include linear polyethylene elastomer, ethylene-α-olefin copolymer elastomer and propylene-α-olefin copolymer elastomer, for example. The α-olefins include α-olefins having a carbon number of 3 to 6 such as propylene, 1-butene, 1-pentene, 1-hexene and 4-methyl-1-pentene, and 1-butene is preferable.

Stylene elastomers include, for example, styrene-ethylene/butylene-stylene block copolymer (SEBS), stylene-butadiene-stylene block copolymer (SBS), stylene-isoprene-stylene block copolymer (SIS), modified SEBS modified by maleic acid or the like, stylene-ethylene/propylene-stylene block copolymer (SEPS), stylene-ethylene/butylene block copolymer (SEB) and stylene-ethylene/propylene block copolymer (SEP).

Urethane elastomers include commercial products such as thermoplastic polyurethane manufactured by Dainichiseika Color & Chemicals Mfg. Co., Ltd. (product name "RESAMINE P") and thermoplastic polyurethane manufactured by KYOWA HAKKO CHEMICAL Co., Ltd. (product name "ESTEN").

In terms of adhesiveness to the other layers (for example, cyclic olefin polymer layer) in the multilayer substrate film and safety as the medical gas barrier film, among the above-mentioned elastomers, polyolefin elastomers are used preferably, and ethylene-α-olefin copolymer elastomers are used more preferably.

From the similar viewpoint, a mixture of the above-mentioned elastomer, linear polyethylene having a density of 0.910 to 0.930 $cm^3$ and high-density polyethylene having a density of 0.950 to 0.970 $cm^3$, in which the linear polyethylene and the high-density polyethylene are mixed in the entire elastomer layer by 20 to 30 weight % and 3 to 10 weight %, respectively, may be used for the elastomer layer.

The ratio of the elastomer layer (when two or more elastomer layers are provided, the sum of each elastomer layer) to the multilayer substrate film in thickness is preferably 55 to 80% and the sum of each elastomer layer to the multilayer substrate film in thickness to the entire medical gas barrier film is 43 to 62%. The thickness of the elastomer layer is preferably 80 to 125 μm.

The heat sealing layer constitutes an innermost layer when the medical bag is formed using the medical gas barrier film of the present invention.

Materials for the heat sealing layer include polyolefin, for example. Above all, polyethylene is preferable and linear polyethylene having a density of 0.925 to 0.945 $cm^3$ is more preferable.

When a medical bag having a plurality of storage chambers (so-called multi-chamber bag) is formed using the medical gas barrier film of the present invention, it is required that peelable seal is formed at each of partitions separating the storage chambers from each other. In this case, to facilitate formation of peelable seal, a resin such as polypropylene that has a different melting point from the polyethylene and is incompatible with the polyethylene should be mixed to the polyethylene by 10 to 40 weight %.

The ratio of the heat sealing layer to the multilayer substrate film in thickness is preferably 10 to 25% and the ratio of the heat sealing layer to the entire medical gas barrier film in thickness is preferably 8 to 19%. The thickness of the heat sealing layer is preferably 15 to 30 μm.

To improve formability, it is preferred that the polyethylene layer is disposed as an outermost layer in the multilayer substrate film.

Polyethylene forming the polyethylene layer in the multilayer substrate film is not specifically limited. For example, linear polyethylene having a density of 0.930 to 0.950 $cm^3$ or the above-mentioned linear polyethylene to which high-density polyethylene having a density of, 0.950 to 0.970 $cm^3$ is added by 15 to 40 weight % may be used.

The ratio of the polyethylene layer to the multilayer substrate film in thickness is preferably 20 to 30% and the ratio of the polyethylene layer to the entire medical gas barrier film in thickness is 14 to 24%. The thickness of the polyethylene layer is preferably 30 to 50 μm.

The specific example of the multilayer substrate film is not limited to this, but for example, a five-layer laminated body in which a pair of the elastomer layers are disposed on both surfaces of the cyclic olefin polymer layer, the heat sealing layer is disposed on the surface on the opposite side to the adhered surface of one elastomer layer to the cyclic olefin polymer layer and the polyethylene layer is disposed on the surface on the opposite side to the adhered surface of the other elastomer layer to the cyclic olefin polymer layer may be used. Alternatively, a four-layer laminated body having no polyethylene layer may be also used.

The multilayer substrate film may be manufactured by molding resin and elastomer materials forming the laminated body, according to various coextruding methods.

The multilayer substrate film may be formed as a cylindrical inflation film according to an inflation method. In this case, the heat sealing layer needs to be molded so as to be disposed on the inner side of the inflation film.

The medical gas barrier film of the present invention may be manufactured by laminating the multilayer gas barrier film and the multilayer substrate film according to a known method.

As a laminating method, the above-mentioned dry lamination is preferable. Used adhesives include the same adhesives as those used in manufacture of the multilayer gas barrier film.

When the cylindrical inflation film is adopted as the multilayer substrate film, the multilayer gas barrier film may be laminated on both the right and back surfaces of the cylindrical multilayer substrate film in the state of being flatly folded.

Although the thickness of the entire medical gas barrier film is not specifically limited, it is preferably 180 to 240 μm, more preferably 190 to 220 μm.

Since the medical gas barrier film has the deposition oriented polyester layer with the inorganic oxide deposited layer and the cyclic olefin polymer layer, excellent gas and vapor barrier properties can be obtained in the medical gas barrier film.

Since (i) with respect to the oriented polyester film as its substrate, the deposited layer of the deposition oriented polyester layer is disposed on the side of the outer surface of the medical bag molded using the medical gas barrier film (that is, the side of the oriented polyamide film layer and polyethylene film layer) not on the side of the inner surface of the medical bag (that is, the side of the multilayer substrate film of the medical gas barrier film), and is protected by the oriented polyamide film layer and the polyethylene film layer, and (ii) since the oriented polyamide layer and the polyethylene layer are disposed between the deposited layer of the deposition oriented polyester layer and the outer surface of the medical bag to ensure enough thickness, even when the medical gas barrier film is subjected to heating and sterilizing treatment under high temperatures, excellent gas and vapor barrier properties can be realized, and furthermore, excellent gas and vapor barrier properties can be maintained while preventing degradation of the deposited layer (deterioration of gas and vapor properties of the medical gas barrier film over time).

Since the medical gas barrier film has the polyethylene layer and the elastomer layer, sufficient flexibility is given to the whole of the film, and especially since the polyethylene layer is provided on the side closer to the film surface than the deposition oriented polyester layer and the oriented polyamide layer, creases and lines can be prevented from occurring on the surface when the infusion solution bag or the like is formed.

Moreover, since the medical gas barrier film has the cyclic olefin polymer layer and the multilayer substrate film containing the cyclic olefin polymer layer is formed without using any adhesive, the compounding ingredients of the film and ingredients of the adhesive can be prevented from eluting from the surface of the heat sealing layer.

The medical bag of the present invention is characterized in that it (I) is formed by welding the medical gas barrier film with the heat sealing layers facing each other, or (II) is formed by welding an open end of the multilayer substrate film in the medical gas barrier film of the present invention in which the multilayer substrate film is formed according to the inflation method.

The above-mentioned medical bag in (I) may be formed in the shape of a bag by superimposing two medical gas barrier films on each other so that their heat sealing layers face each other and heat sealing the circumferential part.

Heat sealing condition in forming the circumferential part is not limited, but is a temperature of 170° C. or higher, preferably 180 to 200° C. for 3 to 5 seconds.

The medical bag of the present invention may be a so-called multi-chamber bag having two or more storage chambers divided by the peelable sealing part.

The heat sealing temperature in forming the peelable sealing part is not limited to this but may be appropriately set so that peel strength of the peelable seal falls between 3.92 to 5.88 N/15 mm, for example, even after the medical bag is subjected to sterilizing treatment under 105 to 115° C. The specific heat sealing condition is set depending on the types of the resin forming the heat sealing layer, but it is, for example, preferably 140 to 155° C., more preferably 140 to 145° C. for 4 to 5 seconds.

The above-mentioned peel strength is measured according to a method "180 degrees peeling method" described in JIS Z 0237 "Adhesive Tape and Adhesive Sheet Test Method". The peel strength is measured as a strength (N/15 mm) at the time when an elastic plastic film having a width of 15 mm is cut with the peelable sealing part as a starting point and a pair of film parts of the measurement sample thus obtained are pulled in the direction of 180 degrees between them at the rate of 200 mm/minute, resulting in peeling of the peelable seal.

According to the present invention, to maintain excellent gas and vapor barrier properties of the medical bag, it is desirable to use a material having excellent gas and vapor barrier properties for a mouth member of the medical bag.

Such mouth member (mouth port, etc.) is, for example, a polyethylene mouth member having an ethylene-vinyl alcohol copolymer (EVOH) layer, a cyclic olefin polymer layer and so on therein.

It is preferred that the medical bag of the present invention is subjected to heating and sterilizing treatment in the state of being filled with a medical fluid and sealed.

According to the medical bag of the present invention, since the medical gas barrier film forming the medical bag has the cyclic olefin polymer layer and the deposited layer of the deposition oriented polyester layer in the multilayer gas barrier film is disposed on the opposite side to the multilayer substrate film and protected by the oriented polyamide layer, even heating and sterilizing treatment under high temperatures is performed, excellent gas and vapor properties can be realized and deterioration of the deposited layer can also be prevented to maintain excellent gas and vapor properties.

Furthermore, according to the medical bag of the present invention, since the medical gas barrier film forming the medical bag has the cyclic olefin polymer layer, and the multilayer substrate film including the cyclic olefin polymer layer is formed without using any adhesive and is disposed on the inner side of the medical bag than the multilayer gas barrier film using the adhesive in lamination, compounding ingredients of the film and ingredients of the adhesive can be prevented from eluting.

EXAMPLES

Next, although the present invention will be described in more detail on the basis of examples and comparative examples, the present invention is not limited by the following examples.

<Manufacture of the Medical Gas Barrier Film and the Medical Bag>

Example 1

(1) Manufacture of a Multilayer Gas Barrier Film

Three layers of an alumina deposition oriented polyester layer 11, an oriented polyamide layer 15 and a polyethylene layer 17 were laminated in this order via adhesive layers (14, 16) formed of the following adhesive according to dry lamination to manufacture a multilayer gas barrier film 10 having a whole thickness of 60 μm (refer to FIG. 1).

In manufacturing the multilayer gas barrier film 10, the oriented polyamide layer 15 was laminated on a surface 11a of a deposited layer 13 of the alumina deposition oriented polyester layer 11 via an adhesive layer 14. The polyethylene layer 17 was laminated on a surface 15b on the opposite side to an adhered surface 15a of the oriented polyamide layer 15 to the deposited layer 13.

Materials used to manufacture the multilayer gas barrier film 10 are as follows:

Alumina deposition oriented polyester film: Alumina is deposited on the biaxial oriented PET film (The whole thickness of the deposited layer 13 and the oriented polyester film 12 is 12 μm and the thickness of the deposited layer 13 is approximately 20 μm. Transparent barrier film manufactured by Toppan Printing Co., Ltd, product name "GLA-AEH")

Oriented polyamide film: Biaxial oriented nylon film (Thickness of 15 μm, manufactured by Unitika Ltd., product name "EMBLEM ONMB")

Polyethylene film: Three-layer co-extrusion film formed of a linear polyethylene 18 having a thickness of 20 μm (density 0.920 g/cm$^3$, MFR 1.0 g/10 minutes (1.90° C.)

manufactured by Mitsui Chemicals, Inc., product name "ULTZEX 2010") and high-density polyethylene 19 and 20 each having a thickness of 5 μm which are disposed on both surfaces of the polyethylene 18 (density 0.950 g/cm$^3$, melt flow rate (MFR) 1.1 g/10 minutes (190° C.), manufactured by Mitsui Chemicals, Inc., product name "HI-ZEX 3300F")

Adhesive: Manufactured by Mitsui Takeda Chemicals, Inc., product name "TAKELAC A 315"

(2) Manufacture of a Multilayer Substrate Film

A cylindrical multilayer substrate film (whole thickness of 160 μm) 22 of five-layer configuration formed of a heat sealing layer 23 having a thickness of 25 μm, a first elastomer layer 24 having a thickness of 55 μm, a cyclic olefin polymer layer 25 having a thickness of 10 μm, a second elastomer layer 26 having a thickness of 55 μm and a polyethylene layer 27 having a thickness of 15 μm, in which the heat sealing layer 23 is disposed on its innermost side, is manufactured (refer to FIG. 1).

Materials for each layer forming the multilayer substrate film 22 are as follows:

The heat sealing layer 23: Linear polyethylene (density 0.930 g/cm$^3$, manufactured by Mitsui Chemicals, Inc., product name "ULTZEX 3020L", MFR 2.1 g/10 minutes (190° C.))

The first elastomer layer 24 and the second elastomer layer 26: Mixed resin of linear polyethylene elastomer (density 0.885 g/cm$^3$, manufactured by Mitsui Chemicals, Inc., product name "TAFMER A0585", MFR 0.5 g/10 minutes (190° C.)) by 70 weight %, linear polyethylene (density 0.920 g/cm$^3$, manufactured by Mitsui Chemicals, Inc., product name "ULTZEX 2010", MFR 1.0 g/10 minutes (190° C.)) by 25 weight % and high-density polyethylene (density 0.965 g/cm$^3$, manufactured by Mitsui Chemicals, Inc., product number "NZ 65150", MFR 16 g/10 minutes (190° C.)) by 5 weight %

The cyclic olefin polymer layer 25: Hydrogenated norbornene ring-opened polymer (product name "ZEONOR 1020R" manufactured by ZEON Corporation, specific gravity 1.01, glass transition temperature (Tg 105° C.))

The polyethylene layer 27: Mixed resin of linear polyethylene (density 0.940 g/cm$^3$, manufactured by Mitsui Chemicals, Inc., product name "ULTZEX 4020L", MFR 2.1 g/10 minutes (190° C.)) by 75 weight % and high-density polyethylene (density 0.965 g/cm$^3$, manufactured by Mitsui Chemicals, Inc., product number "NZ 65150", MFR 16 g/10 minutes (190° C.)) by 25 weight %

(3) Manufacture of the Medical Gas Barrier Film

The right and back surfaces of the multilayer substrate film obtained in the above (2) in the state of being flatly folded (that is, the surface on the side of the polyethylene layer 27 of the multilayer substrate film 22) and the surface on the side of the alumina deposition oriented polyester film of the multilayer gas barrier film obtained in the above (1) (the surface 11b on the opposite side to the deposited layer 13) were laminated via a layer 21 formed of the above-mentioned adhesive according to dry lamination.

In this manner, a cylindrical medical gas barrier film having the layer configuration shown in FIG. 1.

(4) Manufacture of a Medical Bag

Figure 2:
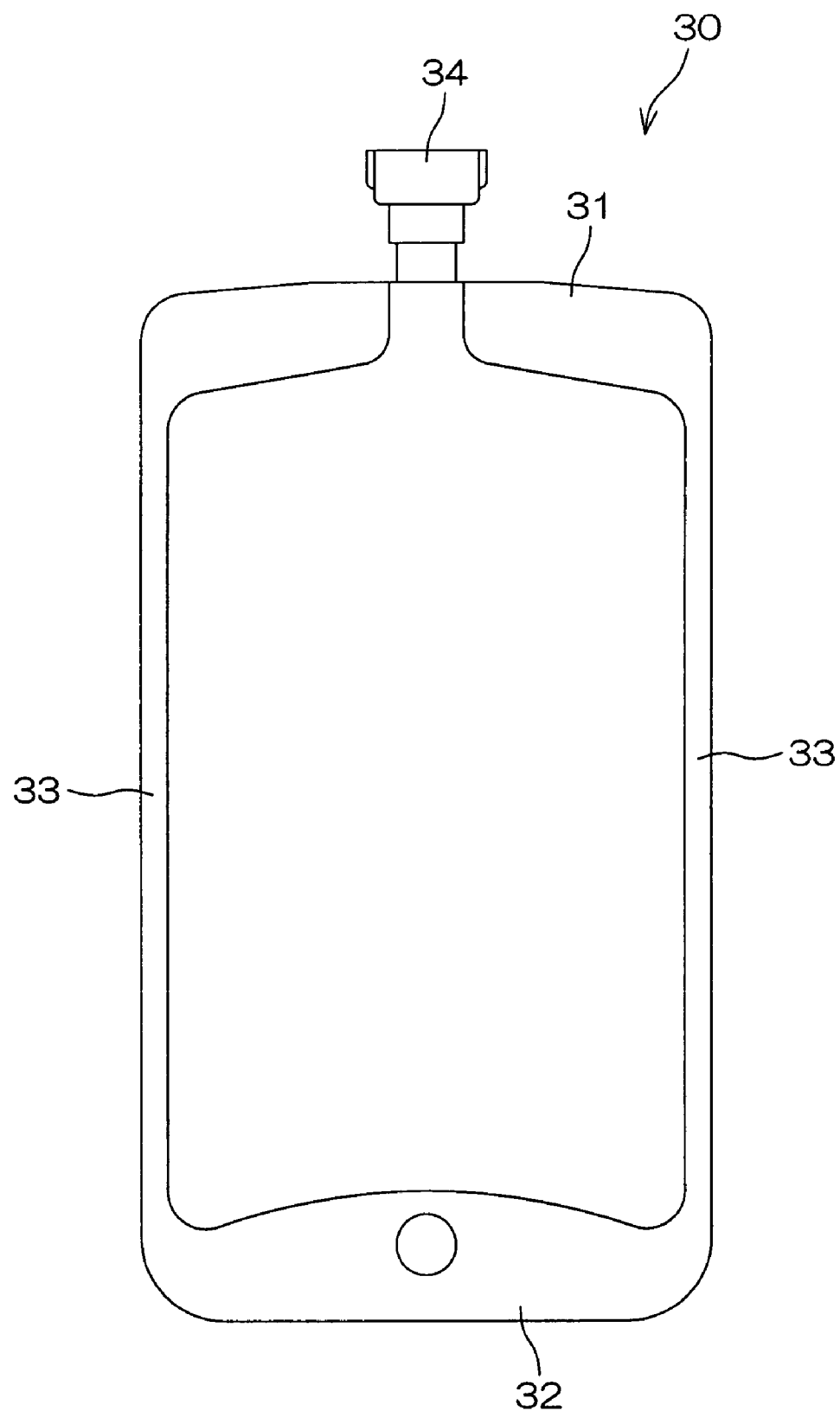
FIG. 2 is a front view showing a medical bag in accordance with an embodiment.

One open end 31 of the cylindrical medical gas barrier film obtained in the above (3) was heat sealed with a below-mentioned mouth member 34 being sandwiched and the other open end 32 and a circumferential part 33 of the multilayer gas barrier film laminated on the surface of the multilayer substrate film were heat sealed to obtain a medical bag 30 shown in FIG. 2.

A mouth port 34 formed of polyethylene and having a layer of ethylene-vinyl alcohol copolymer (EVOH) in the middle thereof was used as the mouth member. The open ends 31 and 32 and the circumferential part (joint part of the multilayer gas barrier film laminated on the surface of the multilayer substrate film) 33 of the medical gas barrier film were heat sealed at 170° C. for 4.5 seconds. Following preheating at 740° C., the mouth port 34 was fixed via the medical gas barrier film by heat sealing at 160° C. for 4.5 seconds.

A storage chamber of the medical bag 30 was filled with distilled water of 500 ml and sealed.

Example 2

(1) Manufacture of a Multilayer Gas Barrier Film

A multilayer gas barrier film was prepared in the same manner as (1) of Example 1.

(2) Manufacture of a Multilayer Substrate Film

A multilayer substrate film was manufactured in the same way as (2) of Example 1 except that, in place of the heat sealing layer (thickness of 25 μm) 23 of Example 1, mixed resin of linear polyethylene (density 0.940 g/cm$^3$, manufactured by Mitsui Chemicals, Inc., product name "ULTZEX 4020L", MFR 2.1 g/10 minutes (190° C.)) by 85 weight % and polypropylene (density 0.910 g/cm$^3$, manufactured by Mitsui Chemicals, Inc., product number "J103WA") by 15 weight % was used as the heat sealing layer.

(3) Manufacture of a Medical Gas Barrier Film

A medical gas barrier film was prepared in the same way as (3) of Example 1 except that the multilayer substrate film obtained in the above (2) was used as the multilayer substrate film in place of the film prepared in Example 1.

(4) Manufacture of a Medical Bag

Figure 3:
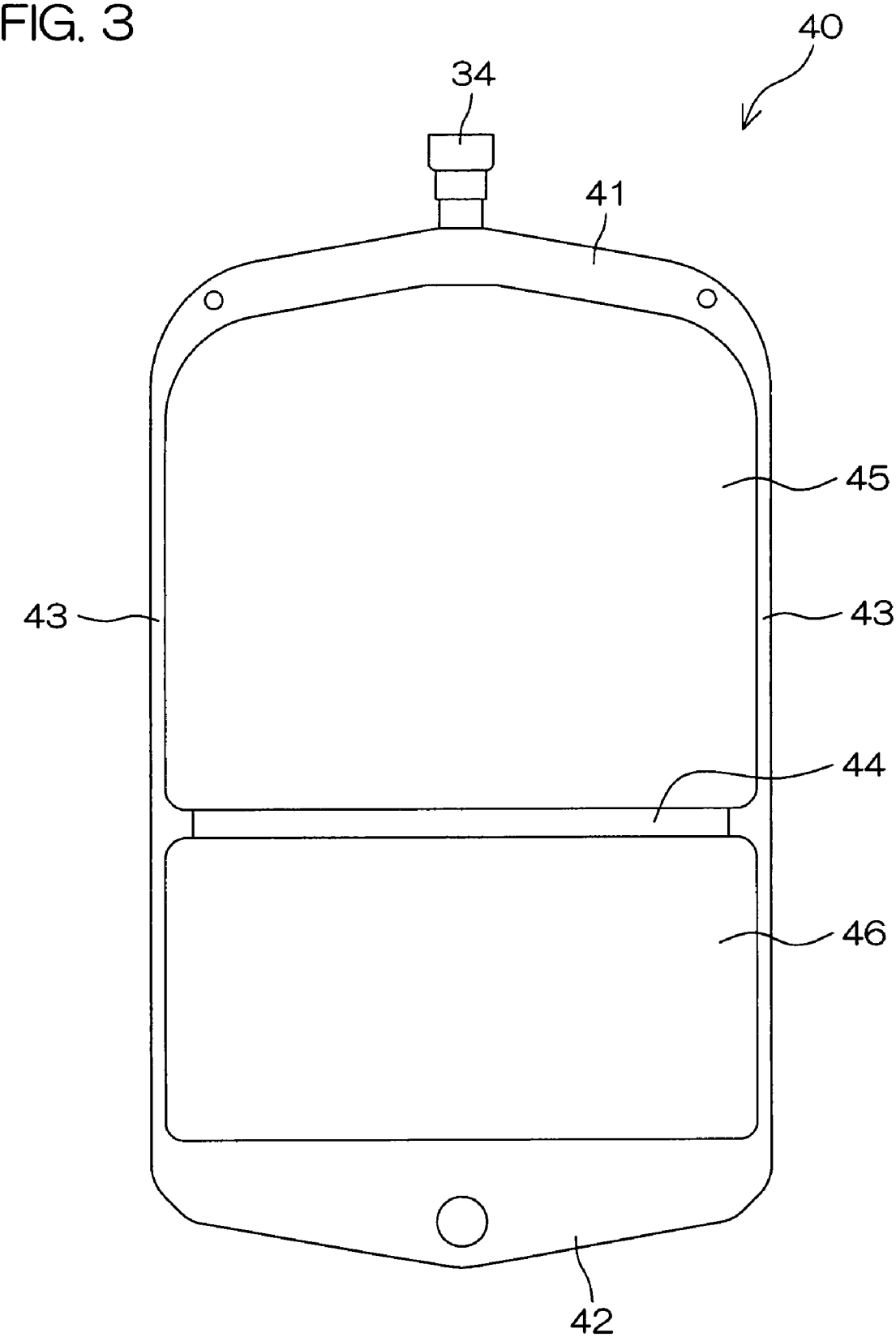
FIG. 3 is a front view showing a medical bag in accordance with another embodiment.

One open end 41 of the cylindrical medical gas barrier film obtained in the above (3) was heat sealed in the state of sandwiching the same mouth member (mouth port 34) as that used in Example 1, the other open end 42 and a joint part (circumferential part) 43 of the multilayer gas barrier film laminated on the surface of the multilayer substrate film were heat sealed and further a peelable sealing part 44 was formed in a storage chamber of a medical bag to obtain a medical bag (multi-chamber bag) 40 shown in FIG. 3.

The open ends 41 and 42 and the circumferential part (joint part of the multilayer gas barrier film laminated on the multilayer substrate film) 43 of the medical gas barrier film were heat sealed at 170° C. for 4.5 seconds and the peelable sealing part 44 was heat sealed at 130° C. for 4.5 seconds. Following preheating at 740° C., the mouth port was fixed via the medical gas barrier film by heat sealing at 160° C. for 4.5 seconds.

A large storage chamber 45 of the medical bag 40 was filled with distilled water of 700 ml and a small storage chamber 46 was filled with distilled water of 300 ml and the both chambers 45 and 46 were sealed.

Comparative Example 1

A medical gas barrier film was manufactured in the same manner as in Example 1 except that the cyclic olefin polymer layer 25 is not provided in the multilayer substrate film 22 of the medical gas barrier film having the layer configuration shown in FIG. 1. The medical bag shown in FIG. 2 was manufactured in the same manner as in Example 1 except that the medical gas barrier film thus obtained was used.

Comparative Example 2

A medical gas barrier film was manufactured in the same manner as in Example 1 except that, in the deposition oriented polyester layer 11 of the multilayer gas barrier film 10 in the medical gas barrier film having the layer configuration shown in FIG. 1, the direction of laminating the oriented polyester film 12 and the deposited layer 13 was reversed. The medical bag shown in FIG. 2 was manufactured in the same manner as in Example 1 except that the medical gas barrier film thus obtained was used.

Comparative Example 3

A medical gas barrier film was manufactured in the same manner as in Example 1 except that the polyethylene layer 17 of the multilayer gas barrier film was not provided and the thickness of the oriented polyamide layer was 30 μm in the medical gas barrier film having the layer configuration shown in FIG. 1. The medical bag shown in FIG. 2 was manufactured in the same manner as in Example 1 except that the medical gas barrier film thus obtained was used.

<Physical Properties Evaluation of the Medical Bag>
(1) Elution Test, Etc.

The medical bags obtained in Examples 1 and 2 and Comparative examples 1 to 3 were subjected to high pressure steam sterilizing treatment (110° C., 60 minutes) and then test pieces were cut.

Using the test pieces thus obtained, an "acute toxicity test", a "sensitization test" and a "hemolysis test" in conformance with rules of The Japanese Pharmacopoeia ($14^{th}$ revision), Part 1 "55. Test Methods for Plastic Containers—2. Extraction Test" and "55. —7. Cytotoxicity Test" and The Japanese Pharmacopoeia ($14^{th}$ version), Part 2 "13. Plastic Containers for Pharmaceutical Products" (Guideline on Basic Biological Tests of Medical Devices and Biomedical Materials, I. Cytotoxicity Test 10. Cytotoxicity Test Using Medical Devices and Extraction Liquid of Materials, II. Sensitization Test and VII. Hemolysis Test) were performed.

(2) Measurement of Transparency, Oxygen Transmission Rate, Etc.

Further, using the test pieces, tests according to The Japanese Pharmacopoeia ($14^{th}$ revision), Part 1 "55. Test Methods for Plastic Containers—4. Transparency Test" and "55. —5. Water Vapor Permeability" were performed, and oxygen transmission rate and sterilization shrinkage rate were measured.

Oxygen transmission rate ($cm^3/m^3/day$) was measured under the conditions of temperature of 20° C. and humidity of 60% RH using an oxygen transmission rate measuring device (manufactured by MOCON Inc. (US), model name "OXTRAN 2/20").

Oxygen transmission rate is preferably 0.2 $cm^3/m^3$/day or less, more preferably 1 $cm^3/m^3$/day or less.

Sterilization shrinkage rate (%) calculated by comparing test pieces cut from the medical bag before being subjected to high pressure steam sterilizing treatment with the abovementioned test pieces in length shows the rate at which the medical gas barrier film is shrunk due to high pressure steam sterilizing treatment.

Sterilization shrinkage rate is preferably 2.5% or less, more preferably 1.0% or less, in MD and preferably 2.5% or less, more preferably 1.0% or less, in TD.

(3) Prop Test 15 medical bags obtained in each of Example 1 and 2 and Comparative example 1 to 3 were subjected to high pressure steam sterilizing treatment (110° C., 60 minutes) and then, five medical bags of each example were stacked in the state of being horizontally arranged, contained in an outer housing and stored at 0° C. for two days. After storage, the medical bags were dropped from the height of 120 cm and occurrence of leakage of liquid and presence or absence of gas and vapor barrier properties reduction were confirmed.

With respect to gas and vapor barrier properties, oxygen transmission rate and vapor transmission rate after the drop test were measured in the same manner as the above-mentioned manner and when oxygen transmission rate exceeded 0.2 $cm^3/m^3$/day and vapor transmission rate exceeded 0.27 $g/m^3$/day, it was regarded that gas and vapor barrier properties were deteriorated.

(4) Evaluation Results

The medical bags in Examples 1 and 2 satisfied reference values of all evaluation items in the tests (1). On the contrary, in the medical bag in Comparative example 1, elution of substances of the adhesive was found.

It found that the medical bags in Examples 1 and 2 had transparency of 82.5%, oxygen transmission rate of 0.04 $cm^3$/$m^3$/day (20° C., 60% RH), vapor transmission rate of 0.18 $g/m^3$/day (40° C., 90% RH), and sterilization shrinkage rate of 1.3 (MD) and −0.3 (TD), and showed excellent gas and vapor properties and extremely low shrinkage rate after sterilization treatment. On the contrary, it was found that the medical bags in Comparative examples 2 and 3 had increased oxygen transmission rate and vapor transmission rate by sterilization treatment and the medical bags in Comparative example 3 had lowered transparency by sterilization treatment.

In the medical bags in Examples 1 and 2, even after the drop test was performed, no leakage of liquid was found and oxygen transmission rate and vapor transmission rate hardly changed. On the contrary, in the medical bags in Comparative example 2 contained in two of three outer housings, leakage of liquid was generated. Even in the medical bags generating no leakage of liquid, increase in oxygen transmission rate and vapor transmission rate was observed. In the medical bags in Comparative example 3, drop of flexibility and resulting occurrence of creases and lines were observed.

The present invention is not limited to the above-mentioned descriptions and can be variously modified in design as long as it falls within the scope of matters stated in claims.

While the present invention has been described by way of the embodiments thereof, these embodiments are merely illustrative, but not limitative of the invention. Variations of the present invention apparent to those skilled in the art are to fall within the scope of the present invention defined by the appended claims.

INDUSTRIAL APPLICABILITY

The medical gas barrier film of the present invention is suitable for a material for medical bags for storing medicine which is easy to deteriorate due to gas such as oxygen, vapor and the like in medical applications.

The medical bag of the present invention is suitable for medical applications, especially for storing medicine which is easy to deteriorate due to gas such as oxygen, vapor and the like.

The invention claimed is:

1. A medical gas barrier film comprising a multilayer gas barrier film and a multilayer substrate film adhered to the multilayer gas barrier film, wherein
the multilayer gas barrier film has a three-layer structure consisting of three layers, which structure includes a deposition oriented polyester layer having a deposited layer of alumina on one surface thereof, an oriented polyamide layer adhered to a surface of the deposited layer of alumina on the one surface of the deposition oriented polyester layer and a polyethylene layer adhered to a surface of the oriented polyamide layer on the opposite side to the surface of the oriented polyamide layer adhered to the deposited layer of alumina, the multilayer substrate film has a five-layer structure formed by laminating a heat sealing layer, a first elastomer layer, a cyclic olefin polymer layer, a second elastomer layer and a polyethylene layer in this order, and a surface of the multilayer substrate film on the side of the polyethylene layer is adhered to a surface of the deposition oriented polyester layer of the multilayer gas barrier film opposite to said one surface of the deposition oriented polyester layer.

2. A medical gas barrier film as stated in claim 1, wherein a total thickness of the first elastomer layer and the second elastomer layer is 55 to 80% of a thickness of the multilayer substrate film.

3. A medical gas barrier film as stated in claim 1, wherein a thickness of the polyethylene layer of the multilayer gas barrier film is 1 or 2 times larger than a total thickness of the deposition oriented polyester layer and the oriented polyamide layer.

4. A medical gas barrier film as stated in claim 1, wherein the polyethylene layer of the multilayer gas barrier film is a three-layer film formed of a linear polyethylene film having a density of 0.910 to 0.930 g/cm$^3$ and high density polyethylene films each having a density of 0.950 to 0.970 g/cm$^3$ and adhered to both surfaces of the linear polyethylene layer, and a thickness of each of the high density polyethylene films is 0.2 to 0.3 times larger than that of the linear polyethylene film.

5. A medical gas barrier film as stated in claim 1, wherein the multilayer substrate film is a cylindrical film formed by inflation molding and an innermost layer of the cylindrical film is the heat sealing layer.

6. A medical bag formed by welding a medical gas barrier film so that heat sealing layers thereof face each other, wherein the medical gas barrier film comprises a multilayer gas barrier film and a multilayer substrate film adhered to the multilayer gas barrier film, the multilayer gas barrier film has a three-layer structure consisting of three layers, which structure includes a deposition oriented polyester layer having a deposited layer of alumina on one surface thereof, an oriented polyamide layer adhered to a surface of the deposited layer of alumina on the one surface of the deposition oriented polyester layer and a polyethylene layer adhered to a surface of the oriented polyamide layer on the opposite side to the surface of the oriented polyamide layer adhered to the deposited layer of alumina, the multilayer substrate film has a five-layer structure formed by laminating a heat sealing layer, a first elastomer layer, a cyclic olefin polymer layer, a second elastomer layer and a polyethylene layer in this order, and a surface of the multilayer substrate film on the side of the polyethylene layer is adhered to a surface of the deposition oriented polyester layer of the multilayer gas barrier film opposite to said one surface of the deposition oriented polyester layer.

7. A medical bag formed by welding an open end of a multilayer substrate film of a medical gas barrier film, wherein the medical gas barrier film comprises a multilayer gas barrier film and a multilayer substrate film adhered to the multilayer gas barrier film, the multilayer gas barrier film has a three-layer structure consisting of three layers, which structure includes a deposition oriented polyester layer having a deposited layer of alumina on one surface thereof, an oriented polyamide layer adhered to a surface of the deposited layer of alumina on the one surface of the deposition oriented polyester layer and a polyethylene layer adhered to a surface of the oriented polyamide layer on the opposite side to the surface of the oriented polyamide layer adhered to the deposited layer of alumina, the multilayer substrate film is a cylindrical film formed by inflation molding and has a five-layer structure formed by laminating a heat sealing layer, a first elastomer layer, a cyclic olefin polymer layer, a second elastomer layer and a polyethylene layer in this order, a surface of the multilayer substrate film on the side of the polyethylene layer is adhered to a surface of the deposition oriented polyester layer of the multilayer gas barrier film opposite to said one surface of the deposition oriented polyester layer, and an innermost layer of the cylindrical multilayer substrate film is the heat sealing layer.

8. A medical bag as stated in claim 6, the whole of which is subjected to heating and sterilization after being filled with a medical fluid and sealed.

9. A medical bag as stated in claim 7, the whole of which is subjected to heating and sterilization after being filled with a medical fluid and sealed.

* * * * *